Figure 1:
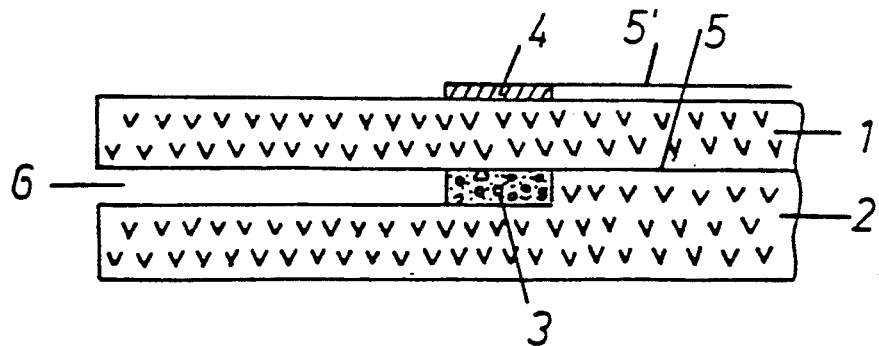

United States Patent [19]

Friese et al.

[11] Patent Number: 5,137,615
[45] Date of Patent: Aug. 11, 1992

[54] SENSOR ELEMENT FOR LIMITING CURRENT SENSORS FOR DETERMINATION OF THE λ VALUE OF GAS MIXTURES

[75] Inventors: Karl-Hermann Friese, Leonberg; Gerhard Hoetzel, Stuttgart, both of Fed. Rep. of Germany

[73] Assignee: Robert Bosch GmbH, Stuttgart, Fed. Rep. of Germany

[21] Appl. No.: 566,376
[22] PCT Filed: Feb. 23, 1989
[86] PCT No.: PCT/DE89/00102
 § 371 Date: Aug. 30, 1990
 § 102(e) Date: Aug. 30, 1990
[87] PCT Pub. No.: WO89/08840
 PCT Pub. Date: Sep. 21, 1989

[30] Foreign Application Priority Data

Mar. 18, 1988 [DE] Fed. Rep. of Germany ....... 3809154

[51] Int. Cl.⁵ .............................................. G01N 27/00
[52] U.S. Cl. ................. 204/424; 204/429; 204/432; 204/410; 204/425
[58] Field of Search ............ 204/424, 429, 432, 410, 204/425

[56] References Cited

U.S. PATENT DOCUMENTS

| | | | |
|---|---|---|---|
| 4,347,113 | 8/1982 | Fischer et al. | 204/195 S |
| 4,579,643 | 4/1986 | Mase et al. | 204/427 |
| 4,645,572 | 2/1987 | Nishizawa | 204/1 T |
| 4,647,364 | 3/1987 | Mase et al. | 204/427 |
| 4,657,659 | 4/1987 | Mase et al. | 204/410 |
| 4,670,128 | 6/1987 | Mase et al. | 204/427 |
| 4,728,411 | 3/1988 | Mase et al. | 204/425 |
| 4,875,981 | 10/1989 | Usami et al. | 204/1 T |
| 4,902,400 | 2/1990 | Usami et al. | 204/426 |
| 4,908,575 | 3/1990 | Usami et al. | 327/711 |
| 4,935,119 | 6/1990 | Yamada et al. | 204/425 |

*Primary Examiner*—John Niebling
*Assistant Examiner*—Arun S. Phasge
*Attorney, Agent, or Firm*—Frishauf, Holtz, Goodman & Woodward

[57] ABSTRACT

A sensor element for limiting current sensors for determination of the λ-value of gas mixtures is proposed, which has at least one outer pumping electrode and one inner pumping electrode, on a solid electrolyte in platelet or foil form, conducting $O^{2-}$ ions, of which the inner pumping electrode is arranged in a diffusion channel for the measuring gas. It consists of a porous three-dimensional precious metal electrode having a supporting structure, the thickness of which electrode corresponds to the height of the diffusion channel. Characteristic of the inner pumping electrode is a greatly improved load-bearing capacity in comparison with electrodes of sheet-like design, whereby the service life of the sensor element is increased. A further advantage of the three-dimensional design of the inner pumping electrode is that it takes on a supporting function during lamination in the production of the sensor element by ceramic foil and screen printing techniques.

11 Claims, 1 Drawing Sheet

SENSOR ELEMENT FOR LIMITING CURRENT SENSORS FOR DETERMINATION OF THE λ VALUE OF GAS MIXTURES

PRIOR ART

The present invention relates generally to limiting current sensors. In the case of such sensor elements, which operate on the diffusion limiting current principle, the diffusion limiting current is measured with a constant voltage applied to the two electrodes of the sensor element. In an exhaust gas produced in combustion processes, this current is dependant on the oxygen concentration as long as the diffusion of the gas to the pumping electrode determines the speed of the reaction taking place. It is known to construct such sensors operating on the polarographic measuring principle in such a way that both anode and cathode are exposed to the gas to be measured, the cathode having a diffusion barrier, in order to achieve an operation in the diffusion limiting current range.

The known limiting current sensors serve as a rule for determination of the λ value of gas mixtures which designates the "total oxygen/oxygen required for complete combustion of the fuel" relationship of the air/fuel mixture burning in a cylinder, the sensors determining the oxygen content of the exhaust gas via an electrochemical pumping current measurement.

On the basis of a simplified and inexpensive production method, in recent years the production of sensor elements which can be produced by ceramic foil and screen printing techniques has established itself in practice.

Planar sensor elements can be produced in a simple and cost-effective way, starting with oxygen-conducting solid electrolytes in platelet or foil form, for example from stabilized zirconium dioxide, which are coated on both sides with an inner and an outer pumping electrode with associated conductor tracks. The inner pumping electrode is in this case advantageously located in the edge region of a diffusion channel, through which the measuring gas is fed, and which serves as gas diffusion resistance.

German Offenlegungsschrift 3,543,759, YAMADA, as well as EP-A 0,142,993, EP-A 0,188,900 and EP-A 0,194,082 also disclose sensor elements and detectors, which have in common that they each have a pumping cell and a sensor cell, which consist of oxygen-conducting solid electrolytes in platelet or foil form and two electrodes arranged thereupon, and have a common diffusion channel.

A disadvantage of sensor elements of the generic type of the main claim is that the front part of the inner pumping electrode, facing the fed measuring gas, is subjected to greater stress than the rear part of the pumping electrode, facing away from the fed measuring gas. This leads to a high electrode polarization, which requires a high pumping voltage. The latter in turn entails the risk of an electrolyte decomposition in the region of the inner pumping electrode.

It is therefore proposed in German Offenlegungsschrift 3,728,618, in a sensor element for limiting current sensors for determination of the λ value of gas mixtures with outer and inner pumping electrodes arranged on a solid electrolyte in platelet or foil form, conducting $O^{2-}$ ions, of which the inner pumping electrode is arranged on the solid electrolyte in platelet or foil form in a diffusion channel for the measuring gas, as well as with conductor tracks for the pumping electrodes, to arrange in the diffusion channel on the side opposite the inner pumping electrode at least a second inner pumping electrode, which is short-circuited with the first inner pumping electrode.

ADVANTAGES OF THE INVENTION

The sensor element according to the invention with the characterizing features of the main claim has, in comparison, the advantage that, due to the special design of the inner pumping electrode, its load-bearing capacity is increased by virtue of its greater electrode area and the service life of the sensor element is improved. A further advantage arises from the fact that the inner pumping electrode takes on a supporting function during lamination and compression in the case of production of the sensor element by ceramic foil and screen printing techniques.

The sensor element according to the invention can be used instead of known sensor elements of planar structure in limiting current sensors of the usual type. Coming into consideration in this case are broadband sensors ($\lambda \gtrless 1$) and lean sensors ($\lambda > 1$). The sensor element according to the invention can consequently be designed solely as a pumping cell, if appropriate with a heating element, for example as a lean sensor for diesel engines, and as such installed in a usual sensor housing, for example of the type known from German Offenlegungsschriften 3,206,903 and 3,537,051, and are used for measurement of the fuel/air ratio in a lean exhaust gas. However, the sensor element according to the invention can also have, apart from the pumping cell, in addition a sensor cell (Nernst cell), which is provided with an additional air reference channel and the one electrode of which is arranged in the region of the pumping electrode in the diffusion channel of the pumping cell and the other electrode of which is located in the air reference channel and is used for measurement of the fuel/air ratio in a lean or rich exhaust gas.

DRAWING

Advantageous embodiments of sensor elements according to the invention are represented in the drawing.

FIG. 1 is a diagrammatic, greatly enlarged representation of a section through a sensor element according to the invention, which can be produced by ceramic foil and screen printing techniques. It consists essentially of the ceramic foils 1 and 2, onto which the inner three-dimensional pumping electrode 3 and the outer pumping electrode 4 have been printed, along with associated conductor tracks 5, 5', by the screen printing method and which are laminated together, creating the diffusion channel 6 forming a tunnel, by means of a usual interlaminar binder. In an advantageous way, the outer pumping electrode 4 and the associated conductor track 5' are covered by a porous cover layer (not shown), for example of Mg-spinel.

Figure 2:
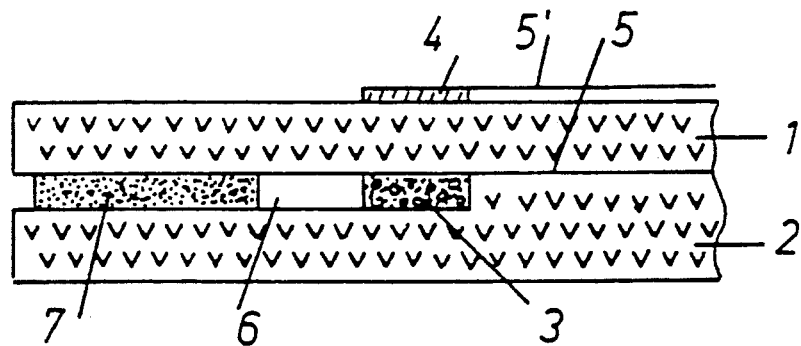

The sensor element represented diagrammatically in FIG. 2 differs from the sensor element represented in FIG. 1 merely in that in the diffusion channel 6 there is provided a porous filling 7, which serves as diffusion barrier for the measuring gas.

Figure 3:
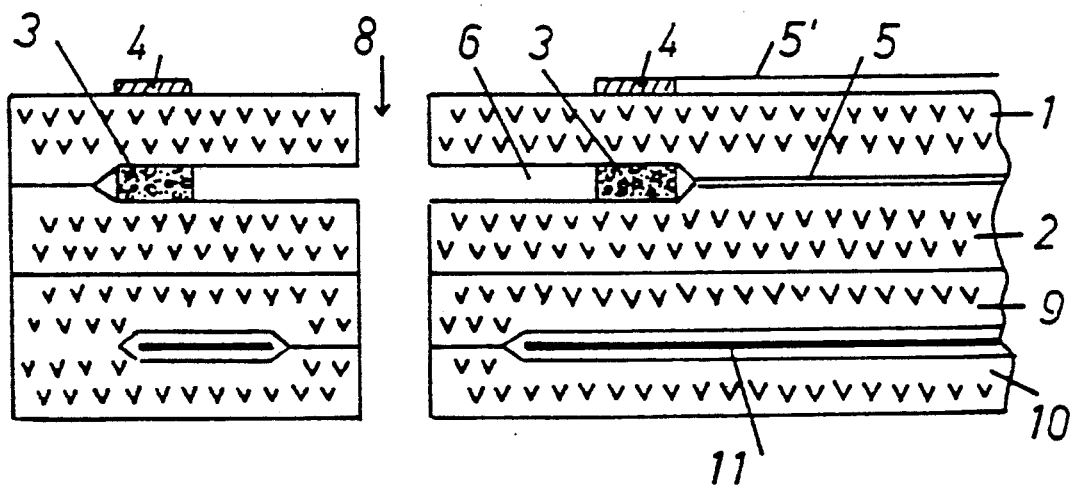

FIG. 3 is a further diagrammatic, greatly enlarged representation of a section through another advantageous embodiment of a sensor element according to the invention, which can be produced by ceramic foil and screen printing techniques, in which the inner three-dimensional pumping electrode 3 and the outer pumping electrode 4 are arranged annularly around the measuring gas feed 8. It consists essentially of four laminated-together solid electrolyte foils 1, 2, 9 and 10 with the punched-out measuring gas feed 8, the annular outer pumping electrode 4 and the three-dimensional inner pumping electrode 3, arranged in the diffusion channel 6. In the case of the embodiment represented in FIG. 3, the sensor element also has a heater 11. However, the foils 9 and 10 with the heater are not absolutely necessary. The annular electrodes 3 and 4 are connected to conductor tracks 5 and 5', which are insulated with respect to the solid electrolyte foils by means of insulating layers (not shown in the drawing), for example $Al_2O_3$ layers. The conductor tracks are connected to a voltage source (not shown), for example a battery with a constant operating voltage in the range from 0.5 to 1.0 volt. In an advantageous way, the outer pumping electrode 4 and the associated conductor track 5' are in turn covered by a porous cover layer (not shown), for example of magnesium spinel.

Solid electrolytes which conduct oxygen ions and are suitable for the production of sensor elements according to the invention are, in particular, those based on $ZrO_2$, $HfO_2$, $CeO_2$ and $ThO_2$. The use of platelets and foils of zirconium dioxide stabilized with yttrium (YSZ) has proved particularly advantageous.

In this case, the platelets and foils preferably have a thickness of 0.25 to 0.3 mm.

The outer pumping electrode 4 preferably consists of a metal of the platinum group, in particular platinum, or of alloys of metals of the platinum group or alloys of metals of the platinum group with other metals. If appropriate, the electrode may also contain a ceramic supporting structure material, such as is also used for the production of the inner pumping electrode. In contrast to the inner pumping electrode 3, designated here as "three-dimensional", the outer pumping electrode 4 however represents rather a more sheet-like two-dimensional electrode, i.e. an electrode of the usual type, which as a rule is thinner than the inner pumping electrode and preferably has a thickness of 8 to 15 μm.

The inner three-dimensional pumping electrode 3 preferably consists of a mixture of a metal of the platinum group, in particular platinum, or of an alloy, as can also be used for producing the outer pumping electrode, and a supporting structure material, such as for example zirconium dioxide stabilized with $Y_2O_3$. If appropriate, the metal of the platinum group may be fully or partially substituted by an electron-conductive metal or metal oxide, such as for example $TiO_2$ or perovskite, or by a mixed-conductive (i.e. electrode (sic)—conductive and ion-conductive) metal oxide, such as for example $CeO_2$ or other oxides of rare earths as well as mixed oxides such as for example uranium-scandium oxides. The proportion by volume of supporting structure material is expediently around 20 to 60%, preferably around 35 to 45%. It has also proved advantageous if the degree of porosity of the inner pumping electrode is around 10 to 40%. At least one part of the pores has in this case preferably a pore diameter of greater than 1 μm. The average pore diameter of the inner pumping electrode is in this case preferably around 2 to 10 μm. The porous supporting structure can in this case be produced by the use of known pore-forming powders, which are added to the mixture, for producing the electrode, of metal component and supporting structure component as well as other usual additives, and are burned or vaporized during the production of the sensor element. Typical pore formers which can be used with success are, for example, theobromine and carbon black as well as carbonates. The pore size of the supporting structure can in this case be controlled by the particle size of the pore-forming powder used. However, the use of pore formers is not absolutely necessary. Rather, it is also possible, for example, to produce a porous supporting structure by use of a supporting structure material with comparatively low sintering activity. The compounds used for producing the electrodes can be prepared by usual known methods and applied to, preferably printed onto, the solid electrolytes in platelet or foil form.

The inner three-dimensional pumping electrode 3 preferably lies directly opposite the outer pumping electrode 4. It may cover the same area, a smaller area or greater area of the solid electrolyte than the outer pumping electrode 4. The inner pumping electrode 3 may accordingly only fill a comparatively small part of the diffusion channel 6 or a comparatively large part of the diffusion channel 6.

According to a particularly advantageous development of the invention, the inner pumping electrode 3 takes up only a part of the space of the diffusion channel 6 and a diffusion barrier 7 is arranged in the diffusion channel 6 ahead of the inner pumping electrode 3, as diagrammatically represented by way of example in FIG. 2.

Such a diffusion barrier consists of a porous material, i.e. a material which does not yet sinter compactly at the sintering temperature of the substrate, for example ZrO substrate, a material for example of coarse-grained $ZrO_2$, Mg-spinel or $Al_2O_3$ with a grain size of, for example, about 10 μm. To create an adequate porosity, if appropriate pore formers may be added, for example thermal carbon black powder, which bakes thoroughly in the sintering process, theobromine or ammonium carbonate. According to a particularly advantageous development of the invention, a channel system for a mixed diffusion of Knudsen and gas phase diffusion, acting as a diffusion barrier for the measuring gas, may be arranged ahead of the inner pumping electrode 3. This channel system may, for example, consist of porously filled diffusion channels for a Knudsen diffusion and hollow channels for a gas phase diffusion. Such channel systems acting as diffusion barriers for the measuring gas are described in more detail in German Offenlegungsschrift 3,728,289.

For the purpose of improvement of the measuring accuracy, the diffusion barrier may, in an advantageous way, contain platinum or a platinum alloy or another catalytically acting metal, in order to achieve an equilibrium adjustment of the gas going into the diffusion channel. The proportion by volume of catalytically acting metal or metal alloy may be around 10 to 90%. The diffusion barrier may take up the entire space of the diffusion channel left free by the inner pumping electrode 3 or only a part of the same. Thus, for example, a free space may also remain between the inner pumping electrode 3 and the diffusion barrier 7. Like the inner pumping electrode 3, the diffusion barrier 7 may be produced in an advantageous way by a thick-film technique.

The conductor tracks 5 and 5', belonging to the pumping electrodes 3 and 4, preferably likewise consist of platinum or a platinum alloy. Pumping electrodes and conductor tracks may be applied to the solid electrolyte body by means of known methods, for example by screen printing. Between the conductor track connecting the outer pumping electrode to a voltage source (not shown in the drawing) and the solid electrolyte carrier, as a rule there is located an insulating layer, for example of $Al_2O_3$. It may, for example, have a thickness of about 15 μm. The inner conductor track is preferably insulated from the solid electrolyte carrier in a similar way. The joining of the individual foils or platelets forming the sensor element may take place by means of a method usual in ceramic foil and screen printing techniques, in which the foils are brought together and heated to temperatures of about 100° C. In this case, the diffusion channel can be prepared at the same time. In an advantageous way, the latter is incorporated by a thick-film technique, for example by a theobromine screen printed layer, the theobromine being vaporized during the subsequent sintering process. Thermal carbon black powders, which bake thoroughly during the sintering process, or ammonium carbonate, which vaporizes, can likewise be used for example for producing the diffusion channel.

If the diffusion channel is to have a porous diffusion barrier, instead of a theobromine screen printed layer, for example a layer of theobromine or of another vaporizable or combustible material and a material which does not yet sinter compactly at the applied sintering temperature of the solid electrolyte substrate, for example coarse-grained $ZrO_2$, magnesium spinel or $Al_2O_3$ with a grain size of, for example, 10 μm, may be used.

EXAMPLE

For the production of a sensor element of the type represented diagrammatically in FIG. 3, foils with a layer thickness of 0.3 mm of zirconium dioxide stabilized with yttrium were used. The applying of the outer pumping electrode 4, consisting of platinum, and of the inner platinum supporting structure electrode 3 to the carrier foils took place by the known screen printing technique, an about 20 μm thick, $Al_2O_3$ insulating layer having being applied in advance to the surface of the carrier foil 1 carrying the outer pumping electrode 4, in the region of the conductor track 5' of the outer pumping electrode 4. The conductor track 5 was also insulated with corresponding insulating layers. The annular pumping electrodes 3 and 4 had an outside diameter of 2.8 mm and an inside diameter of 1.4 mm with a thickness of the outer pumping electrode of 12 μm and of the inner pumping electrode of 40 μm. The inner pumping electrode was produced starting with a screen printing compound which corresponded to the compound used for producing the outer pumping electrode, with the difference that it contained such a quantity of $ZrO_2$ stabilized with $Y_2O_3$ that a degree of electrode porosity of about 30% was achieved. The conductor tracks were produced starting with a usual Pt cermet paste of 85 parts by weight of Pt powder and 15 parts by weight of YSZ powder. The diffusion channel 6 was incorporated by a thick-film technique by a theobromine screen printed layer, the theobromine being vaporized during the subsequent sintering process in the temperature range of around 300° C., leaving behind an about 30 μm high and 1.3 mm deep annular gap. The central measuring gas feed orifice had a diameter of 0.25 mm. After the printing of the carrier foils, i.e. after applying the electrodes, conductor tracks, insulating layers and, if appropriate, a cover layer to the outer pumping electrode, the foils, once joined together, were subjected to a sintering process, in which they were heated for about 3 hours to a temperature in the range of 1380° C.

For the production of a further sensor element with a heater, as represented diagrammatically in FIG. 3, before heating, further foils were laminated to a printed-on heater.

The sensor elements produced were installed in the sensor housing of the type known from German Offenlegungsschriften 3,206,903 and 3,537,051 and used for measurement of the fuel/air ratio in lean and rich exhaust gases.

We claim:

1. Sensor element for limiting-current sensors for determination of the lambda value of exhaust gases of internal combustion engines, which sensor element has
    at least one outer (4) pumping electrode and
    at least one inner (3) pumping electrode on an $O^2$-ion-conductive solid electrolyte, of which the inner pumping electrode is arranged on the solid electrolyte in a diffusion channel (6) defined therein for a measuring gas, said channel having a predetermined height defined perpendicular to a major planar surface of said solid electrolyte,
    as well as conductor tracks for the pumping electrodes,
    wherein
    the inner pumping electrode (3) arranged in the diffusion channel (6), consists essentially of a three-dimensional porous electrode of a metal compound selected from the group consisting of platinum and a metal oxide compound, said inner electrode having a supporting structure and having a thickness sufficient to substantially fill the height of the diffusion channel (6).

2. Sensor element according to claim 1, wherein the height of the diffusion channel (6), and consequently the thickness of the inner pumping electrode (3), is in a range between about 30 and about 100 micrometers.

3. Sensor element according to claim 1, wherein the inner pumping electrode (3) comprises a three-dimensional platinum electrode having a supporting structure.

4. Sensor element according to claim 3, wherein the platinum in the electrode is at least partially replaced by a metal compound which is conductive of at least electrons.

5. Sensor element according to claim 1, wherein the inner pumping electrode has a degree of porosity in a range between about 10% and about 40%.

6. Sensor element according to claim 1, wherein the average pore diameter of the inner pumping electrode (3) is in a range between about 2 and about 100 micrometers.

7. Sensor element according to claim 1, wherein a porous diffusion barrier (7) is arranged ahead, in the direction of diffusion of gas being measured, of the inner three dimensional pumping electrode (3) in the diffusion channel (6).

8. Sensor element according to claim 7, wherein the porous diffusion barrier (7) consists essentially of platinum, for equilibrium adjustment of the gas mixture going into the diffusion channel (6).

9. Sensor element according to claim 1, wherein the sensor element is produced by ceramic foil and screen printing techniques.

10. Sensor element according to claim 1, wherein an outer pumping electrode (4) is provided and the outer pumping electrode and the inner pumping electrode (3) are arranged annularly around a measuring gas feed.

11. Sensor element according to claim 7, wherein the diffusion barrier (7) has a channel system for a mixed diffusion of Knudsen- and gas-phase-diffusion.

* * * * *